United States Patent
Smets et al.

(10) Patent No.: US 8,460,792 B2
(45) Date of Patent: *Jun. 11, 2013

(54) MICROCAPSULE AND METHOD OF PRODUCING SAME

(75) Inventors: Johan Smets, Lubbeek (BE); Radhakrishnan Janardanan Nair, Kobe (JP); An Pintens, Brasschaat (BE); Takuya Yasuhara, Saitama (JP); Takashi Iwasaki, Saitama (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/015,227

(22) Filed: Jan. 27, 2011

(65) Prior Publication Data

US 2011/0123582 A1    May 26, 2011

Related U.S. Application Data

(63) Continuation of application No. 11/526,505, filed on Sep. 25, 2006, now Pat. No. 7,901,772.

(60) Provisional application No. 60/720,861, filed on Sep. 27, 2005.

(51) Int. Cl.
*A61K 8/11* (2006.01)
*A61K 7/50* (2006.01)
*A61K 7/46* (2006.01)
*C11D 3/60* (2006.01)

(52) U.S. Cl.
USPC ............. 428/402.2; 428/402; 428/402.21; 424/401; 424/70.16; 510/130; 510/475; 510/349

(58) Field of Classification Search
USPC ............ 424/493, 497, 451; 347/20; 423/338; 428/402–402.24, 407, 403, 423.1, 474.4; 427/389.9, 213.3–213.36; 264/53, 41, 4–4.7; 521/57, 56, 76, 142
See application file for complete search history.

(56) References Cited

U.S. PATENT DOCUMENTS

| | | | |
|---|---|---|---|
| 4,087,376 A | 5/1978 | Foris et al. | |
| 4,145,184 A | 3/1979 | Brain et al. | |
| 4,430,243 A | 2/1984 | Bragg | |
| 5,066,419 A * | 11/1991 | Walley et al. | 510/396 |
| 5,137,646 A | 8/1992 | Schmidt et al. | |
| 5,324,444 A | 6/1994 | Berry et al. | |
| 5,434,069 A * | 7/1995 | Tsaur et al. | 510/530 |
| 5,486,303 A | 1/1996 | Capeci et al. | |
| 5,489,392 A | 2/1996 | Capeci et al. | |
| 5,516,448 A | 5/1996 | Capeci et al. | |
| 5,565,422 A | 10/1996 | Del Greco et al. | |
| 5,569,645 A | 10/1996 | Dinniwell et al. | |
| 5,574,005 A | 11/1996 | Welch et al. | |
| 5,576,282 A | 11/1996 | Miracle et al. | |
| 5,591,146 A * | 1/1997 | Hasse | 604/359 |
| 5,595,967 A | 1/1997 | Miracle et al. | |
| 5,597,936 A | 1/1997 | Perkins et al. | |
| 5,691,297 A | 11/1997 | Nassano et al. | |
| 5,879,584 A | 3/1999 | Bianchetti et al. | |
| 6,225,464 B1 | 5/2001 | Hiler, II et al. | |
| 6,306,812 B1 | 10/2001 | Perkins et al. | |
| 6,326,348 B1 | 12/2001 | Vinson et al. | |
| 6,849,591 B1 | 2/2005 | Boeckh et al. | |
| 7,901,772 B2 | 3/2011 | Smets et al. | |
| 2003/0050346 A1 | 3/2003 | Hsu | |
| 2003/0125222 A1 * | 7/2003 | Jahns et al. | 510/130 |
| 2004/0087477 A1 | 5/2004 | Ness | |
| 2005/0089540 A1 * | 4/2005 | Uchiyama et al. | 424/401 |
| 2005/0276831 A1 | 12/2005 | Dihora et al. | |

FOREIGN PATENT DOCUMENTS

| | | |
|---|---|---|
| EP | 0 251 446 A2 | 1/1988 |
| EP | 1 602 713 A1 | 12/2005 |
| JP | 09-000911 | 1/1997 |
| WO | WO 91/06637 | 5/1991 |
| WO | WO 95/10591 | 4/1995 |
| WO | WO 00/32601 | 6/2000 |
| WO | WO 2005/042532 A1 | 5/2005 |

OTHER PUBLICATIONS

Knovel Critical Tables, Second Edition, 2003.
Chinese Patent Office, Office Action dated May 28, 2010 in reference to co-pending Chinese Application No. 200680043700.2.

* cited by examiner

*Primary Examiner* — James J Seidleck
*Assistant Examiner* — S. Camilla Pourbohloul
(74) *Attorney, Agent, or Firm* — Marianne Dressman; Andrew J. Mueller

(57) ABSTRACT

A microcapsule which is able to stably retain a benefit agent such as a volatile substance for an extended period, and which is also suitable for encapsulating fragrances and the like. Such capsule encapsulates a mixture comprising a volatile substance, and an additive that has a higher melting point than the volatile substance and is able to undergo mutual dissolution with the volatile substance, wherein the mixture exhibits a melting point range, and a portion of, or all of, that melting point range falls within a range from −20 to 60° C. The present invention also relates to consumer products including cleaning and/or treatment compositions comprising such microcapsules, and processes of making and using same.

10 Claims, No Drawings

MICROCAPSULE AND METHOD OF PRODUCING SAME

RELATED APPLICATIONS

The present application claims priority under 35 U.S.C. §119 of U.S. application Ser. No. 11/526,505 filed Sep. 25, 2006 which is a non-provisional of U.S. application Ser. No. 60/720,861 filed Sep. 27, 2005, both of which are incorporated by reference herein in their entirety.

FIELD OF THE INVENTION

The present invention relates to a microcapsule that encapsulates a volatile substance such as a fragrance, and a method of producing such a microcapsule. The present invention also relates to consumer products comprising such microcapsules, and processes of making and using same.

BACKGROUND OF THE INVENTION

Various benefit agents, such fragrances, are expensive and/or difficult to deliver as neat liquids as they exhibit high volatility, and rapidly lose their aroma if left exposed to the atmosphere. As a result, fragrances have been microcapsulated. That is, sealed inside a capsule, to enable the aroma to be retained. However, even if a benefit agent such as a highly volatile fragrance is sealed within a microcapsule, the fragrance still can escape through gaps within the microcapsules cell wall. Thus, long term storage, particularly in the presence of other materials, is a problem. A technique described in Japanese Laid-Open Publication No. Hei 9-911, wherein a volatile substance is encapsulated by incorporation within a gel-like polyurethane resin, attempts to solve this problem. In this technique, during the capsulation process, a polyfunctional isocyanate and a polyol are reacted together to produce a gel-like polyurethane resin, and the volatile substance is incorporated within this polyurethane resin. Thus, while not being bound by theory, it is believed that release of the volatile substance from the capsule core is suppressed. Unfortunately such technique employs isocyanate which can produce an irritating odor that detracts from benefit agents, particularly the aroma of the fragrance. In addition, improvement is also desirable in terms of the fact that the proportion of the polyurethane resin in the encapsulated material at the core is quite high relative to the quantity of the target volatile substance. Such an improved microcapsule is particularly desirable as consumers typically associate the odor of a cleaned or treated article with the degree of cleanliness or freshness of such article.

Accordingly, the present invention provides a microcapsule which is able to stably retain a volatile substance for an extended period, in the presence of other materials, such as consumer product formulations. Such microcapsule is particularly suitable for encapsulating fragrances and the like. In addition, consumer products, including cleaning and/or treatment compositions that contain the aforementioned microcapsules and processes of making and using same are disclosed

SUMMARY OF THE INVENTION

The present invention relates to a microcapsule which encapsulates a mixture comprising a volatile substance, and an additive that has a higher melting point than the volatile substance and is able to undergo mutual dissolution with the volatile substance, wherein the mixture exhibits a melting point range, and a portion of, or all of, the melting point range falls within a range from −20 to 60° C.

According to one embodiment, a consumer product comprising a resin microcapsule is provided. The microcapsule encapsulates a homogenous mixture comprising a volatile substance and an additive mutually dissolved within the volatile substance, wherein the additive has a melting point that is at least equal to or greater than 25° C., wherein the melting point of the additive is greater than a melting point of the volatile substance, and wherein the homogenous mixture has a melting point range such that at least a portion of the melting point range is between about 0° C. and about 60° C. such that the homogenous mixture is in a semisolid state from about 0° C. to about 60° C.

The present invention also relates to consumer products including cleaning and/or treatment compositions comprising such microcapsules, and processes of making and using same.

DETAILED DESCRIPTION OF THE INVENTION

Definitions

As used herein consumer products include articles and cleaning and treatment compositions.

As used herein, the term "cleaning and/or treatment composition" includes, unless otherwise indicated, granular or powder-form all-purpose or "heavy-duty" washing agents, especially laundry detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, laundry bars, mouthwashes, denture cleaners, car or carpet shampoos, bathroom cleaners; hair shampoos and hair-rinses; shower gels and foam baths and metal cleaners; as well as cleaning auxiliaries such as bleach additives and "stain-stick" or pre-treat types.

As used herein, the phrase "is independently selected from the group consisting of . . . " means that moieties or elements that are selected from the referenced Markush group can be the same, can be different or any mixture of elements.

As used herein, the articles "a" and "an" when used in the specification or a claim, are understood to mean one or more of what is claimed or described.

The test methods disclosed in the Test Methods Section of the present application must be used to determine the respective values of the parameters of Applicants' inventions.

Unless otherwise noted, all component or composition levels are in reference to the active level of that component or composition, and are exclusive of impurities, for example, residual solvents or by-products, which may be present in commercially available sources.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

Microcapsules

In a volatile substance-encapsulated microcapsule according to the present invention, a mixture is formed at the core in which the additive that has a higher melting point than the volatile substance is mutually dissolved with the volatile substance. By forming a mixture of the volatile substance and the additive in this manner, the melting point, boiling point, and volatilization temperature of the volatile substance are adjusted, enabling the volatility of the volatile substance to be suppressed to low levels.

As a result, release of the volatile substance inside the microcapsule is suppressed, enabling stable retention and sustained release of the volatile substance over an extended period.

In addition, because the range of possible additives is broad, an additive can be selected in accordance with the properties of the volatile substance. For example, an odorless additive can be selected in the case of a fragrance, meaning it is possible to form a huge variety of encapsulated substances.

A microcapsule according to the present invention (hereafter also referred to as simply a "capsule") encapsulates a mixture (hereafter also referred to as the "encapsulated material" or "encapsulation material") comprising a volatile substance, and an additive that has a higher melting point than the volatile substance and is able to undergo mutual dissolution with the volatile substance.

Because the volatile substance and the additive are able to undergo mutual dissolution, the mixture exists as a homogenous substance of the two substances. This mixture exhibits a melting point range ($T1$-$T2$, wherein $T1<T2$), and either a portion of, or all of, this melting point range falls within a range from −20 to 60° C. This includes those cases where at least one, or perhaps both, of the lower limit temperature $T1$ and the upper limit temperature $T2$ of this melting point range fall within the range from −20 to 60° C., and those cases where the melting point range $T1$-$T2$ is broader than the range from −20 to 60° C., and includes the entire range from −20 to 60° C.

In other words, the possible cases include (1) $T1<-20°$ C.$<T2<60°$ C. (wherein only $T2$ falls within the specified range), (2) $-20°$ C.$\leq T1<T2\leq 60°$ C. (wherein both $T1$ and $T2$ fall within the specified range), (3) $-20°$ C.$<T1<60°$ C.$<T2$ (wherein only $T1$ falls within the specified range, and (4) $T1<-20°$ C. and $60°$ C.$<T2$ (wherein $T1$-$T2$ includes the entire specified range from −20 to 60° C.).

Including the melting point ($T3$) of the volatile substance, and the melting point ($T4$, wherein $T3<T4$) of the additive, yields the relationship $T3<T1<T2<T4$.

Within this melting point range ($T1$-$T2$), the mixture adopts a state in which solid and liquid coexist. In this description, this state is referred to as a "semisolid" state. In other words, the melting point range described above is the temperature range over which the mixture exists as a semisolid.

At temperatures higher than $T2$, (a) the mixture is a homogenous solution (liquid). When the temperature is lowered gradually to less than $T2$, (b) a solid starts to gradually precipitate out of the solution, producing a semisolid state. As the temperature is lowered further, (c) the solid portion gradually increases, (d) the fluidity falls, producing a sorbet-like state, and then (e) the entire mixture develops rigidity. Finally, when the temperature falls below $T1$, (f) the mixture becomes completely solid. By gradually lowering the temperature in this manner, the state of the mixture can be changed (a)→(b)→(c)→(d)→(e)→(f), and the term "semisolid" refers to all of these states except for (a) and (f).

$T2$ refers to the temperature at which solid material, no matter how small, starts to become visible within the liquid (the temperature at which visual inspection no longer reveals a liquid free of solids). $T1$ refers to the temperature at which fluidity disappears (or the temperature at which fluidity commences). The existence or absence of fluidity is determined by bringing a cylindrical glass rod with a cross-sectional diameter of 7 mm (wherein the tip of the rod has been cut through the cross section to generate a flat end face) into perpendicular contact with the surface of a mixture inside a container (a 100 ml beaker), applying a load of 700 gf, and observing whether or not the tip of the glass rod penetrates into the mixture. Accordingly, $T1$ refers to the temperature at which the glass rod is no longer able to penetrate (or the temperature at which the rod is first able to penetrate) the mixture.

The measurements of $T2$ and $T1$ are conducted by first converting the mixture to a liquid, and then observing the changes in state as the temperature is gradually lowered.

Although the solid that first begins to precipitate as the temperature is gradually lowered comprises predominantly the higher melting point component, namely the additive, it is thought that the solid also incorporates a portion of the volatile substance. It is thought that as the temperature is lowered, the proportion of the volatile substance within the solid increases. In contrast, although the liquid phase within the semisolid comprises mostly the volatile substance, it is thought that the liquid also incorporates a portion of the additive. In other words, although the proportions of the solid component and the liquid component within the semisolid, and the respective compositions of the two components vary depending on the temperature, it is believed that the fact that the solid component and the liquid component co-exist within the melting point range enables the stability of the volatile substance to be improve.

The melting point range for pure substances is usually quite narrow, whereas the melting point range for mixtures is often much broader. In the case of mixtures of substances with a large difference in melting points, even wider melting point ranges can be obtained.

In the present invention, the volatile substance itself is often a mixture of organic compounds with different melting points, and addition of the additive produces a mixture of even more compounds, meaning a mixture with a broader melting point range is obtained.

The broadening of the melting point range for the mixture in this manner is advantageous in the present invention. In the semisolid state, an equilibrium is maintained between volatilization and retention of the volatile substance, enabling both volatilization and retention to be achieved in a favorable balance.

In order to suppress the volatility of the volatile substance, either a portion of, or all of, the melting point range for the mixture must fall within a range from −20 to 60° C., and preferably falls within a range from −10 to 55° C. In addition, cases in which either a portion of, or all of, the melting point range for the mixture falls within a range from 0 to 50° C., which represents the temperature band in which normal human life is conducted, is even more desirable. The reason for this desirability is that if the upper limit temperature T2 for the semisolid state is lower than 0° C., then the encapsulated material comprising the volatile substance will be liquid under normal usage conditions, increasing the danger that the volatility will be unable to be adequately suppressed, whereas in contrast, if the lower limit temperature T1 for the semisolid state exceeds 50° C., then the encapsulated material comprising the volatile substance will be completely solid under normal usage conditions, increasing the danger that the volatility will be overly suppressed, meaning the effect of the volatile substance will not manifest adequately.

Furthermore, if the upper limit temperature T2 for the melting point range is 60° C. or lower, so that the mixture is liquid at temperatures exceeding 60° C., then a further benefit is obtained in that when an in situ polymerization method is selected as the microcapsulation method described below, the capsulation can be completed easily at a temperature of 60 to 80° C.

In other words, cases in which the melting point range satisfies either (1) $T1<-20°$ C.$<T2<60°$ C., or (2) $-20°$ C.$\leq T1<T2\leq 60°$ C. are preferred. Alternatively, T2 is preferably within a range from 40 to 60° C., and even more preferably from 40 to 55° C., and most preferably from 40 to 50° C.

On the other hand, the lower limit temperature T1 for the melting point range is preferably 30° C. or lower, and even more preferably 20° C. or lower, and most preferably 10° C. or lower. Although there are no particular lower limits for T1, considering normal usage conditions and the need to achieve the required melting point range, T1 values of at least −10° C. suffice, and values of −20° C. or greater are quite satisfactory.

In addition, the difference between T1 and T2 (the melting point range) is preferably at least approximately 10° C., and preferably at least approximately 20° C., even more preferably at least approximately 30° C., even more preferably at least approximately 40° C., and is most preferably 50° C. or greater.

In the present invention, in addition to the sustained release effect obtained as a result of the microcapsulation, the fact that the encapsulated material is in a semisolid state enables the storage stability and sustained releasability of the volatile substance to be improved dramatically.

Furthermore, because the encapsulated material is a semisolid, the membrane strength relative to external pressure can be increased compared with the case of a liquid material. As a result, a capsule of adequate strength can be formed even if the proportion of the capsule accounted for by the membrane material (the cell material or the wall material) is reduced, and the proportion of the encapsulated material is increased.

Generally when microcapsules are dispersed within a liquid solvent such as a liquid ink, a liquid cosmetic, or a liquid cleaning agent or the like, there is a danger that solvent passing through the capsule membrane and penetrating the capsule interior may cause a deterioration in the stability of the volatile substance. Moreover, in those cases where the encapsulated material is a liquid, the encapsulated material is prone to passing through the capsule membrane and being eluted into the external phase.

In contrast, in the present invention, the volatile substance is incorporated within a semisolid-state mixture, meaning the properties of the volatile substance can be stably maintained, even under this type of attack by an external solvent, and elution of the encapsulated material into the external phase can be prevented, thus providing improved stability relative to the capsule external phase.

In addition, because a portion of the high-cost volatile substance can be replaced with a comparatively low-cost additive within the encapsulated material, the present invention is also advantageous from a cost perspective.

Examples of suitable volatile substances include a variety of reagents (active ingredients) that exhibit volatility, including the various fragrances, plant-based essential oils, deodorants, deodorizers, repellents, insect repellents, insecticides, and agricultural chemicals, and the present invention is suited to any of these materials when it is important to enable the effect of the active ingredient to manifest over an extended period. Combinations of two or more of these volatile substances may also be used.

Specific examples of suitable fragrances include animal and plant-based natural fragrances such as musk, civet, castorium, rose, jasmine, orange, lavender, sandalwood, cinnamon, rosemary, lemon, iris, violet, lily of the valley, lily, lime, vanilla, and mint; synthetic versions of these natural fragrances; and synthetic fragrances such as lilac, carnation, cosmos, amaryllis, fragrant olive, tulip, sweet briar, rugosa rose, sasanqua, thistle, camellia, sage, hyacinth, chrysanthemum, cedar, bouquet, citron, kabosu, coffee, curry, garlic, matsutake mushroom, banana, chocolate, yoghurt, watermelon, beef, sauce, and steak.

Of these, oily fragrances are preferred, and fragrances such as orange, grape, grapefruit, apple, strawberry, pineapple, peach, melon, lime, blueberry, lemon, mint, lavender, eucalyptus, rose, rosemary, lily of the valley, lily, freesia, cypress, and white cedar are particularly preferred.

Examples of suitable plant-based essential oils (natural essential oils) include eucalyptus, orange, lavender, lemon, lemongrass, peppermint, tea tree, rosewood, citronella, rosemary, ylang-ylang, bergamot, marjoram, myrtle, chamomile, neroli, jasmine, cinnamon, ginger, thyme, palmarosa, fennel, lime, basil, patchouli, black pepper, and rose absolute.

Examples of suitable repellents and insect repellents include capsaicin, peppermint oil, eucalyptus, cypress, white cedar, menthol oil, allyl isothiocyanate, methyl salicylate, ethyl salicylate, and nonylic acid vanillylamide.

Examples of suitable deodorants and deodorizers include phthalate esters, phosphate esters, plant-based oil extracts, and terpene-based deodorizers.

Examples of suitable agricultural chemicals include fenitrothion, methyl parathion, parathion, diazinon, warfarin, alachlor, pyrethrin, cycloheximide, sethoxydim, and triflumizole.

Examples of suitable insecticides include permethrin, pyrethroid compounds, and fipronil.

There are no particular restrictions on the additive, provided it has a melting point T4 that is higher than the melting point T3 of the volatile substance (namely, T3<T4), is able to undergo mutual dissolution with the encapsulated volatile substance, and on dissolution, is able to form a mixture with a melting point that falls within a range from −20 to 60° C.

For example, provided the additive is a compound with a melting point T4 that falls within a range from 25 to 200° C., preparing a mixture with the volatile substance for which either a portion of, or all of, the melting point range (T1-T2) falls within the above range is comparatively simple, and consequently such additives are preferred. If the additive has a melting point higher than 200° C., then dissolution with the volatile substance may become difficult, depending on the nature of the volatile substance.

In accordance with the usage conditions for the microcapsules, compounds with a melting point T4 that falls within a range from 40 to 120° C., or even more preferably from 50 to 100° C., are particularly desirable.

In terms of the general properties of the additive, the additive itself preferably has either no odor or very little odor, so that in those cases where a fragrance is encapsulated as the volatile substance, the additive does not impair the characteristics of the fragrance. In addition, the use of compounds that are stable under heat and light is also preferred.

From the viewpoints of workability during microcapsulation and solubility in the volatile substance, generally, the additive is preferably a lipophilic compound (with low solubility in water).

Specifically, compounds that contain a hydroxyl group and/or a carboxyl group are preferred, and the use of alcohols, carboxylic acids, or hydroxy acids with melting points within the range from 25 to 200° C. is particularly desirable. Alternatively, the use of paraffin (paraffin hydrocarbons) is also desirable. In addition to these compounds, polymer compounds (such as plastics and unvulcanized rubber) that are capable of dissolution in the volatile substance can also be used.

These additives can be used either alone, or in combinations of two or more different compounds.

Specific examples of suitable alcohols include straight-chain or branched-chain higher aliphatic alcohols with 12 or more carbon atoms, such as lauryl alcohol, myristyl alcohol, palmityl alcohol, cetyl alcohol, stearyl alcohol, 2-octyldodecanol, and behenyl alcohol. Mixed alcohols produced by mixing two or more of these alcohols can also be used.

Alternatively, mixtures of one or more of these alcohols of 12 or more carbon atoms and one or more aliphatic alcohols with less than 12 carbon atoms can also be used favorably.

In addition, the aliphatic alcohol may also be a derivative of a sulfonic acid or phosphoric acid, or a derivative that contains a halogen, nitrogen, sulfur, or phosphorus or the like.

Both aliphatic carboxylic acids and aromatic carboxylic acids can be used as the carboxylic acid, and specific examples of suitable acids include lauric acid, myristic acid, palmitic acid, behenic acid, stearic acid, arachidic acid, ligonceric acid, crotonic acid, elaidic acid, erucic acid, nervonic acid, benzoic acid, and methylbenzoic acid.

An example of a suitable hydroxy acid is salicylic acid.

Suitable paraffin compounds include mixtures containing hydrocarbons with 20 or more carbon atoms. These mixtures may also include hydrocarbons with less than 20 carbon atoms.

There are no particular restrictions on the ratio between the volatile substance and the additive within the mixture, and this ratio is preferably adjusted in accordance with the melting points of the two materials. For example, in those cases where the melting point of the additive is relatively high in relation to the melting point and boiling point of the volatile substance (or those cases where the melting point and boiling point of the volatile substance is relatively low in relation to the melting point of the additive; in other words, those cases where T4-T3 is large), the blend quantity of the additive required to ensure that the melting point of the mixture falls within the specified temperature range is comparatively small. In contrast, in those cases where the melting point of the additive is relatively low in relation to the melting point and boiling point of the volatile substance (or those cases where the melting point and boiling point of the volatile substance is relatively high in relation to the melting point of the additive; in other words, those cases where T4-T3 is small), the additive must be added in a much larger quantity.

Specifically, the blend quantity of the additive is preferably within a range from 10 to 200 parts by weight, and even more preferably from 10 to 100 parts by weight, and most preferably from 20 to 50 parts by weight, per 100 parts by weight of the volatile substance. Particularly in those cases where the volatile substance is a fragrance, in order to ensure adequate manifestation of the aroma, the blend quantity of the additive is preferably no more than 100 parts by weight, that is, within a range from 10 to 100 parts by weight, and is even more preferably from 20 to 50 parts by weight, per 100 parts by weight of the fragrance.

More specifically, the addition of 20 to 50 parts by weight of an additive with a melting point from 50 to 100° C. to 100 parts by weight of the volatile substance, thereby producing a mixture with a melting point that falls within a range from 0 to 50° C. is extremely desirable. This ability to increase the relative blend quantity of the volatile substance within the mixture of a preferred embodiment is one of the characteristic features of the present invention. In such cases, the additive is dissolved in the volatile substance.

The mixture that constitutes the encapsulated material of the microcapsule may also comprise other components in addition to the volatile substance and the additive. Examples of these other components include organic solvents such as toluene, xylene, and hexane, as well as lubricants, dyes, organic and inorganic pigments, antioxidants, ultraviolet absorbers, and other organic compounds.

There are no particular restrictions on the membrane material of the microcapsule, and suitable examples include organic polymer materials such as gelatin, gelatin-gum Arabic, acrylic resins, urethane resins, melamine resins, urea-formalin resins, nylons, polyethers, alginic acid, polyvinyl alcohol, polystyrene, paraffin, and cellulose; and inorganic materials such as titanium dioxide, calcium carbonate, carbon black, silica, alkali earth metals, silicates, iron oxides, cobalt carbonate, and zinc oxide.

Processes of Making Microcapsules

Microcapsulation of the encapsulation material can be conducted using a variety of methods, including interfacial polymerization, in situ polymerization, coacervation, in-liquid drying, spray drying, in-liquid curing, and air suspension. Of these methods, interfacial polymerization, in situ polymerization, and coacervation are preferred, and in situ polymerization methods are particularly desirable.

In those cases where the encapsulation material is oily (an oil phase), the microcapsule may be prepared in an aqueous system.

For example, in situ polymerization includes: preparing an emulsion of a mixture comprising the volatile substance, and the additive that has a higher melting point than the volatile substance and is able to undergo mutual dissolution with the volatile substance; and adding a membrane material to the emulsion and conducting a polymerization, thereby forming a microcapsule which encapsulates the mixture. By using this production method, a microcapsule according to the present invention can be favorably produced.

As follows is a description of a preferred embodiment of the present invention.

First, a volatile substance such as an oily fragrance, and an additive are mixed together at a temperature exceeding the melting point T4 of the additive, thus yielding a mixture in which the two materials are mutually dissolved. A pH regulator is preferably used to adjust pH of the mixture. Examples of acids as the pH regulator include formic acid, acetic acid, citric acid, hydrochloric acid, sulfuric acid, phosphoric acid, nitric acid, tartaric acid, boric acid, and fumaric acid. Examples of alkalis include alkali metal hydroxides, ammonia, and triethanolamine.

While still in a liquid state, this (lipophilic) mixture is then mixed with water, and emulsified, thus preparing an emulsion. During this step, an emulsion accelerator or the like is preferably used to stabilize the oil droplets of the mixture. An anionic water-soluble polymer is preferably used as the emulsion accelerator for microcapsulation. Examples of anionic water-soluble polymers include ethylene-maleic anhydride copolymer, styrene-maleic anhydride copolymer, methylvinyl ether-maleic anhydride copolymer, polyacrylic acid, polystyrenesulfonic acid, acrylic acid-styrenesulfonic acid copolymer, acrylic acid-acrylamide-acrylonitrile ternary copolymer, and acrylic acid-acrylonitrile-acid phosphoxy polyethyleneglycol methacrylate ternary copolymer.

Subsequently, a membrane material (such as a prepolymer) is added to this emulsion, and this membrane material is then polymerized around the periphery of the oil droplets, thus forming the microcapsule walls. This yields a microcapsule slurry. If necessary, the solvent can be removed from the slurry to produce a microcapsule powder.

Emulsification of the mixture can be conducted using a typical emulsification-dispersion device such as a stirrer, homomixer, homodisper, homojetter, colloid mill, ultrasonic dispersion device, or ultrasonic emulsifier. Specific examples of suitable commercially available devices include general stirrers such as the BL-series 3-1 motor stirrers (manufactured by Shinto Scientific Co., Ltd.) and the A520 portable mixer (manufactured by Satake Chemical Equipment Mfg., Ltd.), and general homomixers such as the TK Homomixer Mark II 20 (manufactured by Tokushu Kika Kogyo Co., Ltd.) and the TK Pipeline Homomixer SL (manufactured by Tokushu Kika Kogyo Co., Ltd.).

The above microcapsulation is preferably conducted at a temperature higher than the upper limit temperature (T2) of the melting point range for the mixture, and for example, is preferably conducted with the entire system maintained at a temperature within a range from 60 to 80° C.

Once the capsulation is complete, there are absolutely no problems associated with solid-liquid or liquid-gas phase changes caused by temperature variations within the encapsulated material inside the capsules. This property, wherein the capsules can be treated in the same manner regardless of whether phase changes have occurred within the encapsulated material, is one of the significant advantages of microcapsules.

Suitable examples of the membrane material used during the in situ polymerization include urea resins, melamine resins, acrylate esters, and polyisocyanates. The use of melamine resins (melamine and formaldehyde), urea-formalin resins (urea and formaldehyde) as the membrane material is particularly preferred.

For example, in those cases where a melamine resin is used as the membrane material, the production is preferably conducted in the manner described below. First, the volatile substance and the additive are mixed together at a temperature that exceeds the upper limit temperature (T2) of the melting point range for the mixture to be encapsulated, thus forming an encapsulation material (A) (oil phase). In a separate preparation, in order to enable acceleration and stabilization of the oil droplets of the mixture, ethylene maleic anhydride resin as the emulsion accelerator is dissolved in water, yielding an emulsion accelerator liquid (B). In another preparation, an aqueous solution (C) of a melamine resin prepolymer is also prepared. At a temperature exceeding T2, the material (A) is then mixed with the liquid (B) and emulsified to prepare an emulsion, and a stirring number is adjusted until the desired average particle size is obtained. The solution (C) is then added, and stirring is continued, thereby producing a melamine resin membrane around the periphery of the oil droplets of the encapsulation material, and yielding a microcapsule slurry.

The average particle size of the oil droplets within the emulsified mixture can be set appropriately in accordance with the desired average particle size for the final product microcapsules.

A preferred embodiment in the case of an in situ polymerization using a urea-formalin resin is as described below. First, a urea resin monomer, a resorcin resin monomer, and an ethylene maleic anhydride resin (emulsion accelerator) are dissolved in water. This solution is heated to a temperature exceeding the upper limit temperature (T2) of the melting point range for the mixture to be encapsulated, an encapsulation material (oil phase) prepared in the same manner as described above is then added to the solution and emulsified, and stirring is continued until the desired average particle size is obtained. Formaldehyde is then added, and stirring is continued, thereby producing a urea-formalin resin membrane around the periphery of the encapsulation material, and yielding a microcapsule slurry.

Next is a description of a coacervation method. First, the membrane material is dissolved in a water phase, and the oil phase of the encapsulation material is then added and stirred, thereby dispersing the encapsulation material as fine droplets. To the water phase of the thus obtained O/W dispersion system (emulsion) is gradually added a poor solvent relative to the membrane material (a liquid that is unable to readily dissolve the membrane material), thereby lowering the solubility of the membrane material and causing the membrane material to precipitate out in a manner that encircles the fine droplets. Alternatively, the temperature of the O/W dispersion system may be lowered, thereby lowering the solubility of the membrane material and causing the precipitation.

In the above description, the W/O dispersion system could also be formed by preparing the membrane material as the oil phase and the encapsulation material as the water phase.

In the case of interfacial polymerization, an oil-soluble membrane material monomer and a water-soluble monomer that react together to form the membrane are used. First, an oil phase premix comprising a uniform mixture of the oil-soluble membrane material monomer and the encapsulation material, and a water phase comprising the water-soluble monomer and an emulsion accelerator are prepared. The oil phase premix is then dispersed within the water phase, and the resulting O/W or W/O dispersion system is heated, thereby effecting polymerization at the interface between the oil phase and the water phase.

The particle size of the microcapsules can be selected in accordance with their intended usage. Although there are no particular restrictions, if suitability for a wide variety of potential applications is considered, then the average particle size is preferably within a range from 0.5 to approximately 100 μm. If the particle size is too large, then the capsules themselves become prone to rupture, making them unsuitable for a variety of applications. In contrast, if the particle size is too small, the capsules become overly resistant to rupture, increasing the danger that the effects of the contents may not manifest adequately.

For example, in the case of capsule-containing ink or in those cases where capsules are blended into fibers, paper, or erasers or the like, a small particle size of approximately 1 to 20 μm is preferred in terms of dispersion and processing. In contrast, in applications where capsules are adhered to the surface of a molded product or the like, and the application requires the capsules to be easily ruptured, a large particle size of approximately 20 to 100 μm is preferred in terms of increasing the frequency of contact and lowering the strength of the capsules.

Regardless of whether in situ polymerization, interfacial polymerization, or some other polymerization method is used, the capsule particle size can be controlled by altering factors such as the revolution speed and the shape of the stirring blade or rotor blade of the stirrer or homomixer used during the emulsification step of the microcapsulation process, or by adjusting the reaction rate by altering the polymerization conditions (such as the reaction temperature and time) for the membrane material.

Microcapsules can be used for a variety of applications. Techniques for using the microcapsules include simply adding and dispersing them in the case of liquid materials, or incorporating the microcapsules by coating, spraying, adhesion or kneading techniques in the case of substrates for manufacturing paper or fabrics.

Microcapsules can be used within a wide range of products, and potential applications in those cases where the volatile substance is a fragrance include adding the microcapsules to inks, coating materials (both water-based and oil-based, for pens or spray-type applications, etc.), cosmetics, air fresheners, deodorants, cleaning agents, and fabric softeners and the like; spraying or bonding the microcapsules to printed matter (such as new year greeting cards, catalogues, letter writing paper, and seals), fabrics, textiles, textile products (such as clothing and towels), and tissue paper; and blending or mixing the microcapsules into molded resins, rubber, textiles, and erasers and the like or the raw materials thereof.

The blend quantity of the microcapsules when used in these types of products can be adjusted appropriately in accordance with the desired product characteristics.

Consumer Products

In a first aspect of Applicants' invention, Applicants' invention includes a consumer product such as an article and/or cleaning and/or treatment composition comprising at least 0.00001 weight percent of a benefit agent containing microcapsule according to, any balance of said compositions being one or more adjunct materials.

In a second aspect of Applicants' invention, Applicants' invention includes a consumer product such as an article and/or cleaning and/or treatment composition comprising from about 0.00001 to about 99.9 weight percent, from about 0.00001 to about 10 weight percent, from about 0.02 to about 5 weight percent or even from about 0.2 to about 2 weight percent of a benefit agent containing microcapsule according to the present invention, any balance of said compositions being one or more adjunct materials.

When tested according to test Method 1, the aforementioned aspects of Applicants' may comprise less than or equal to 50 ppm formaldehyde, less than or equal to 25 ppm formaldehyde, less than or equal to 10 ppm formaldehyde or even less than or equal to 5 ppm formaldehyde.

When tested according to test Method 2, the aforementioned aspects of Applicants' invention may comprise at least 5%, from about 5 to about 99%, from about 8 to about 80% or even from about 10 to about 60% water.

If any of the aforementioned aspects of Applicants' invention is an aqueous heavy duty liquid detergent, such detergent may have a pH of from about 2 to about 12, from about 4 to about 10 or even from about 6 to about 9. Otherwise such consumer product may have, when measured by Method 3, a pH of from about 8 to about 12, from about 8.5 to about 11 or even from about 9 to about 11.

Aforementioned aspects of Applicants' invention typically contain an adjunct material that is a surfactant. Such surfactant may be selected from anionic, nonionoic, zwitterionic, cationic and ampholitic surfactants. Anionic surfactants are typically used in liquid detergents in levels of from about 1 to about 80, from about 1 to about 50 or even from about 2 to about 20 percent by weight. A representative list of surfactants can be found in the adjunct materials section of this specification. However, when an anionic surfactant is employed, particularly in a liquid detergent, such as a aqueous liquid detergent, such surfactant may be selected from the group consisting of $C_{11}$-$C_{18}$ alkyl benzene sulfonate (LAS), primary, branched and random $C_{10}$-$C_{20}$ sulfates (AS) and mixtures thereof.

Aforementioned aspects of Applicants' invention may contain a microcapsule of the present invention wherein the encapsulated benefit agent comprises a perfume, or a perfume mixture.

Aforementioned aspects of Applicants' consumer product inventions may include other perfume systems, for example, free perfume, pro-perfumes such as beta-ketoesters, esters, acetals, oxazolidines, ortho-esters, beta-amino ketones and Schiff Bases, perfume containing zeolite systems, and materials such as cyclodextrins.

Adjunct Materials

While not essential for the purposes of the present invention, the non-limiting list of adjuncts illustrated hereinafter are suitable for use in the instant compositions and may be desirably incorporated in certain embodiments of the invention, for example to assist or enhance cleaning performance, for treatment of the substrate to be cleaned, or to modify the aesthetics of the cleaning composition as is the case with perfumes, colorants, dyes or the like. The precise nature of these additional components, and levels of incorporation thereof, will depend on the physical form of the composition and the nature of the cleaning operation for which it is to be used. Suitable adjunct materials include, but are not limited to, surfactants, builders, chelating agents, dye transfer inhibiting agents, dispersants, enzymes, and enzyme stabilizers, catalytic materials, bleach activators, hydrogen peroxide, sources of hydrogen peroide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids, solvents and/or pigments. In addition to the disclosure below, suitable examples of such other adjuncts and levels of use are found in U.S. Pat. Nos. 5,576,282, 6,306,812 B1 and 6,326,348 B1 that are incorporated by reference.

As stated, the adjunct ingredients are not essential to Applicants' compositions. Thus, certain embodiments of Applicants' compositions do not contain one or more of the following adjuncts materials: surfactants, builders, chelating agents, dye transfer inhibiting agents, dispersants, enzymes, and enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids, solvents and/or pigments. However, when one or more adjuncts are present, such one or more adjuncts may be present as detailed below:

Bleaching Agents—The cleaning compositions of the present invention may comprise one or more bleaching agents. Suitable bleaching agents other than bleaching catalysts include photobleaches, bleach activators, hydrogen peroxide, sources of hydrogen peroxide, pre-formed peracids and mixtures thereof. In general, when a bleaching agent is used, the compositions of the present invention may comprise from about 0.1% to about 50% or even from about 0.1% to about 25% bleaching agent by weight of the subject cleaning composition. Examples of suitable bleaching agents include:

(1) photobleaches for example sulfonated zinc phthalocyanine;

(2) preformed peracids: Suitable preformed peracids include, but are not limited to, compounds selected from the group consisting of percarboxylic acids and salts, percarbonic acids and salts, perimidic acids and salts, peroxymonosulfuric acids and salts, for example, Oxzone®, and mixtures thereof. Suitable percarboxylic acids include hydrophobic and hydrophilic peracids having the formula R—(C=O)O—O-M wherein R is an alkyl group, optionally branched, having, when the peracid is hydrophobic, from 6 to 14 carbon atoms, or from 8 to 12 carbon atoms and, when the peracid is hydrophilic, less than 6 carbon atoms or even less than 4 carbon atoms; and M is a counterion, for example, sodium, potassium or hydrogen;

(3) sources of hydrogen peroxide, for example, inorganic perhydrate salts, including alkali metal salts such as sodium salts of perborate (usually mono- or tetra-hydrate), percarbonate, persulphate, perphosphate, persilicate salts and mixtures thereof. In one aspect of the invention the inorganic perhydrate salts are selected from the group consisting of sodium salts of perborate, percarbonate and mixtures thereof. When employed, inorganic perhydrate salts are typically present in amounts of from 0.05 to 40 wt %, or 1 to 30 wt % of the overall composition and are typically incorporated into such compositions as a crystalline solid that may be coated. Suitable coatings include, inorganic salts such as alkali metal silicate, carbonate or borate salts or mixtures thereof, or organic materials such as water-soluble or dispersible polymers, waxes, oils or fatty soaps; and (4) bleach activators having R—(C=O)-L wherein R is an alkyl group, optionally branched, having, when the bleach activator is hydrophobic, from 6 to 14 carbon atoms, or from 8 to 12 carbon atoms and, when the bleach activator is hydrophilic, less than 6 carbon atoms or even less than 4 carbon atoms; and L is leaving group. Examples of suitable leaving groups are benzoic acid and derivatives thereof—especially benzene sulphonate. Suitable bleach activators include dodecanoyl oxybenzene sulphonate, decanoyl oxybenzene sulphonate, decanoyl oxybenzoic acid or salts thereof, 3,5,5-trimethyl hexanoyloxybenzene sulphonate, tetraacetyl ethylene diamine (TAED) and nonanoyloxybenzene sulphonate (NOBS). Suitable bleach activators are also disclosed in WO 98/17767. While any suitable bleach activator may be employed, in one aspect of the invention the subject cleaning composition may comprise NOBS, TAED or mixtures thereof.

When present, the peracid and/or bleach activator is generally present in the composition in an amount of from about 0.1 to about 60 wt %, from about 0.5 to about 40 wt % or even from about 0.6 to about 10 wt % based on the composition. One or more hydrophobic peracids or precursors thereof may be used in combination with one or more hydrophilic peracid or precursor thereof.

The amounts of hydrogen peroxide source and peracid or bleach activator may be selected such that the molar ratio of available oxygen (from the peroxide source) to peracid is from 1:1 to 35:1, or even 2:1 to 10:1.

Surfactants—The cleaning compositions according to the present invention may comprise a surfactant or surfactant system wherein the surfactant can be selected from nonionic surfactants, anionic surfactants, cationic surfactants, ampholytic surfactants, zwitterionic surfactants, semi-polar nonionic surfactants and mixtures thereof. When present, surfactant is typically present at a level of from about 0.1% to about 80%, from about 1% to about 50% or even from about 5% to about 40% by weight of the subject composition.

Builders—The cleaning compositions of the present invention may comprise one or more detergent builders or builder systems. When a builder is used, the subject composition will typically comprise at least about 1%, from about 5% to about 60% or even from about 10% to about 40% builder by weight of the subject composition. Builders include, but are not limited to, the alkali metal, ammonium and alkanolammonium salts of polyphosphates, alkali metal silicates, alkaline earth and alkali metal carbonates, aluminosilicate builders and polycarboxylate compounds, ether hydroxypolycarboxylates, copolymers of maleic anhydride with ethylene or vinyl methyl ether, 1, 3, 5-trihydroxy benzene-2, 4, 6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3, 5-tricarboxylic acid, carboxymethyloxysuccinic acid, and soluble salts thereof.

Chelating Agents—The cleaning compositions herein may contain a chelating agent. Suitable chelating agents include copper, iron and/or manganese chelating agents and mixtures thereof. When a chelating agent is used, the subject composition may comprise from about 0.005% to about 15% or even from about 3.0% to about 10% chelating agent by weight of the subject composition.

Dye Transfer Inhibiting Agents—The cleaning compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Brighteners—The cleaning compositions of the present invention can also contain additional components that may tint articles being cleaned, such as fluorescent brighteners. Suitable fluorescent brightener levels include lower levels of from about 0.01, from about 0.05, from about 0.1 or even from about 0.2 wt % to upper levels of 0.5 or even 0.75 wt %.

Dispersants—The compositions of the present invention can also contain dispersants. Suitable water-soluble organic materials include the homo- or co-polymeric acids or their salts, in which the polycarboxylic acid comprises at least two carboxyl radicals separated from each other by not more than two carbon atoms.

Enzymes—The cleaning compositions can comprise one or more enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, mannanases, pectate lyases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is an enzyme cocktail that may comprise, for example, a protease and lipase in conjunction with amylase. When present in a cleaning composition, the aforementioned enzymes may be present at levels from about 0.00001% to about 2%, from about 0.0001% to about 1% or even from about 0.001% to about 0.5% enzyme protein by weight of the composition.

Enzyme Stabilizers—Enzymes for use in detergents can be stabilized by various techniques. The enzymes employed herein can be stabilized by the presence of water-soluble sources of calcium and/or magnesium ions in the finished compositions that provide such ions to the enzymes. In case of aqueous compositions comprising protease, a reversible protease inhibitor, such as a boron compound, can be added to further improve stability.

Catalytic Metal Complexes—Applicants' cleaning compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra(methylenephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. Nos. 5,597,936; 5,595,967. Such cobalt catalysts are readily prepared by known procedures, such as taught for example in U.S. Pat. Nos. 5,597,936, and 5,595,967.

Compositions herein may also suitably include a transition metal complex of ligands such as bispidones (WO 05/042532 A1) and/or macropolycyclic rigid ligands—abbreviated as "MRLs". As a practical matter, and not by way of limitation, the compositions and processes herein can be adjusted to provide on the order of at least one part per hundred million of the active MRL species in the aqueous washing medium, and will typically provide from about 0.005 ppm to about 25 ppm, from about 0.05 ppm to about 10 ppm, or even from about 0.1 ppm to about 5 ppm, of the MRL in the wash liquor.

Suitable transition-metals in the instant transition-metal bleach catalyst include, for example, manganese, iron and chromium. Suitable MRLs include 5,12-diethyl-1,5,8,12-tetraazabicyclo[6.6.2]hexadecane.

Suitable transition metal MRLs are readily prepared by known procedures, such as taught for example in WO 00/32601, and U.S. Pat. No. 6,225,464.

Solvents—Suitable solvents include water and other solvents such as lipophilic fluids. Examples of suitable lipophilic fluids include siloxanes, other silicones, hydrocarbons, glycol ethers, glycerine derivatives such as glycerine ethers, perfluorinated amines, perfluorinated and hydrofluoroether solvents, low-volatility nonfluorinated organic solvents, diol solvents, other environmentally-friendly solvents and mixtures thereof.

Processes of Making Consumer Products

The products of the present invention can be formulated into any suitable form and prepared by any process chosen by the formulator, non-limiting examples of which are described in Applicants' examples and in U.S. Pat. Nos. 5,879,584; 5,691,297; 5,574,005; 5,569,645; 5,565,422; 5,516,448; 5,489,392; 5,486,303 all of which are incorporated herein by reference. When benefit agent containing microcapsules are incorporated into a consumer product, such microcapsules may need to be further processed. Such processing typically entails homogenizing the liquid capsule slurry by mixing or stirring, adding water to the capsule slurry, adding a structuring agent to the capsule slurry, adjusting the density of the capsule content, adding a dispersant or a anti-sedimentation to the capsule slurry or a mixture thereof. Such processing typically depends on the requirements of the formulation and/or article that will comprise the benefit containing microcapsule. In certain cases the microcapsules may be embedded in a consumer product when the consumer product is produced or formed and/or adhered to the surface of such consumer product by physical and/or chemical means including gluing.

Method of Use

The present invention includes a method for cleaning and/or treating a situs inter alia a surface or fabric. Such method includes the steps of contacting an embodiment of Applicants' consumer product, if a composition in neat form or diluted in a wash liquor, with at least a portion of a surface or fabric then optionally rinsing such surface or fabric. The surface or fabric may be subjected to a washing step prior to the aforementioned rinsing step. For purposes of the present invention, washing includes but is not limited to, scrubbing, and mechanical agitation. As will be appreciated by one skilled in the art, the consumer products of the present invention are ideally suited for use in a variety of applications including cleaning or treating a surface for example in a laundry application. Accordingly, the present invention includes a method for laundering a fabric. The method comprises the steps of contacting a fabric to be laundered with a said cleaning laundry solution comprising at least one embodiment of Applicants' cleaning composition, cleaning additive or mixture thereof. The fabric may comprise most any fabric capable of being laundered in normal consumer use conditions. The solution preferably has a pH of from about 8 to about 10.5. The compositions may be employed at concentrations of from about 500 ppm to about 15,000 ppm in solution. The water temperatures typically range from about 5° C. to about 90° C. The water to fabric ratio is typically from about 1:1 to about 30:1.

Test Methods

Method 1: Formaldehyde is analyzed by means of a derivatization specific to aldehydes and carbonyl compounds. This is accomplished via room temperature derivatization with 2,4-Di Nitro Phenyl Hydrazine (DNPH) prior to a chromatographic separation using Reversed Phase Chromatography with UV/Vis detection (wavelength setting=365 nm). Calibration is performed through "External Standard calibration" with reference formaldehyde solutions made up from commercially available 36-37% Formaldehyde solution. Activity of this material can be determined via a redox titration.

Method 2: ASTM E203-01 via Karl Fischer titration method.

Method 3: pH is determined by Health Canada's method "Determination of the pH of Consumer Products in Aqueous Solution" Product Safety Reference Manual, Book 5—Laboratory Policies and Procedures Effective 2001-10-28 Part B: Test Methods Section, Method C-13 Amendment #29

Method 4. Procedure for Determination of % Perfume Leakage

When determining the % perfume leakage from perfume microcapsules in liquid detergent, a fresh sample of liquid detergent with equal level of free perfume (without Perfume Microcapsules) must also be analysed in parallel for reference.

1. Preparation of Internal Standard Solution
   Stock solution of tonalid: Weigh 70 mg tonalid and add 20 ml hexane p.a.
   Internal Standard Solution solution: Dilute 200 µl of stock solution in 20 ml hexane p.a.
   Mix to homogenize
2. Perfume Extraction from Liquid Detergent without Perfume Microcapsules (Reference)
   Weigh 2 g of liquid detergent product into an extraction vessel
   Add 2 ml of ethanol and 1 ml of deionised water
   Shake gentle to homogenize
   Add 2 ml of Internal Standard Solution and close vessel
   Extract perfume by gently turning the extraction vessel upside-down for 20 times (manually)
   Add spoon tip of Sodium Sulphate
   After separation of layers, immediately transfer hexane-layer into Gas Chromatograph auto sampler-vial and cap vial
   Inject splitless (1.5 µl) into Gas Chromatograph injection-port
   Run Gas Chromatographic-Mass Spectrometric analysis: Gas Chromatographic separation on Durawax-4 (60 m, 0.32 mm ID, 0.25 µm Film) 40° C./4° C./min/230° C./20'
3. Perfume Extraction from Liquid Detergent with Perfume Microcapsules
   Weigh 20 g of liquid detergent product into a centrifuge vessel of 50 ml
   Centrifuge for 5 min at 3500 rpm
   Take 2 g of the liquid layer (lower layer), avoid contact with upper capsules layer
   Add 2 ml of ethanol and 1 ml of deionised water
   Shake gentle to homogenize
   Add 2 ml of Internal Standard Solution and close vessel
   Extract perfume by gently turning the extraction vessel upside-down for 20 times (manually)
   Add spoon tip of Sodium Sulphate
   After separation of layers, immediately transfer hexane-layer into Gas Chromatograph auto sampler-vial and cap vial
   Inject splitless (1.5 µl) into Gas Chromatograph injection-port
   Run Gas Chromatographic-Mass Spectrometric analysis: Gas Chromatographic separation on Durawax-4 (60 m, 0.32 mm ID, 0.25 µm Film) 40° C./4° C./min/230° C./20'
4. Calculation: The Perfume Leakage from Capsules Per Individual Perfume Raw Material:

Area Perfume Raw Material caps×Area Internal Standard Solution ref×Weight ref×100

% perfume leakage=Area Internal Standard Solution caps×Area Perfume Raw Material ref×Weight caps

EXAMPLES

As follows is a more detailed description of the present invention based on a series of examples, although the present invention is in no way restricted to the examples presented below. In the following description, the units "% by weight" and "parts by weight" are abbreviated as "%" and "parts" respectively when referring to microcapsule inventions.

Example 1

Production of Melamine Resin Membrane/Fragrance Microcapsules (in situ Polymerization Method)

(A) Preparation of encapsulation material (mixture): A mixture comprising 75% of a mint fragrance (X-7028, manufactured by Takasago International Corporation, this also applies to all subsequent references to mint) and 25% of palmitic acid (melting point: 63° C.) is stirred at 70° C., thereby dissolving the palmitic acid in the fragrance. The melting point range (T1-T2) for the resulting mixture is from 5 to 45° C. (confirmed visually). The mixture is held at 55° C. to prevent it solidifying prior to emulsification.

(B) Preparation of emulsion accelerator liquid: 15% of ethylene maleic anhydride resin (Scripset-520, manufactured by Monsanto Company) and 85% of water are mixed together at 60° C., and the mixture is adjusted to pH 4 using acetic acid.

(C) Preparation of aqueous solution of melamine resin prepolymer: 15% of a melamine-formaldehyde resin (Sumirez Resin 615K, manufactured by Sumitomo Chemical Co., Ltd.) is dissolved in 85% of water at 60° C.

(D) Capsulation: 100 parts of the above emulsion accelerator liquid (B) is stirred at 60° C. at 3,000 rpm using a TK Homomixer Mark II 20 (manufactured by Tokushu Kika Kogyo Co., Ltd.), 100 parts of the above encapsulation material (A) is added and emulsified, the rotational speed is then gradually raised, and stirring is conducted at 7,000 rpm for 30 minutes, yielding an emulsion in which the average particle size of the oil droplets of the encapsulation material is approximately 3 µm (as measured by a laser diffraction particle size analyzer SALD-3100 (manufactured by Shimadzu Corporation), this analyzer is also used to measure all subsequent particle sizes).

To this emulsion is added 50 parts of the above melamine resin prepolymer aqueous solution (C), and stirring is continued for 2 hours, thus generating a melamine resin membrane around the periphery of the encapsulation material, and forming a microcapsule slurry with a solid fraction concentration of approximately 40%.

Example 2

Production of Melamine Resin Membrane/Fragrance Microcapsules (in situ Polymerization Method)

An encapsulation material (A) is prepared by mixing 75% of the mint fragrance and 25% of behenyl alcohol (melting point: 70° C.) at 75° C., thereby dissolving the behenyl alcohol in the fragrance and forming a mixture. The melting point range for the thus obtained mixture is from 10 to 50° C. The mixture is held at 60° C. to prevent it solidifying prior to emulsification.

With the exception of using this encapsulation material (A), a microcapsule slurry with a solid fraction concentration of approximately 40% is prepared in the same manner as the Example 1.

Example 3

Production of Melamine Resin Membrane/Fragrance Microcapsules (in situ Polymerization Method)

An encapsulation material (A) is prepared by mixing 65% of the mint fragrance and 35% of paraffin wax (EMW-0003, manufactured by Nippon Seiro Co., Ltd., melting point: 50°

C.) at 60° C., thereby dissolving the paraffin wax in the fragrance and forming a mixture. The melting point range for the thus obtained mixture is from 0 to 40° C. The mixture is held at 50° C. to prevent it solidifying prior to emulsification.

With the exception of using this encapsulation material (A), a microcapsule slurry with a solid fraction concentration of approximately 40% is prepared in the same manner as the example 1.

Example 4

Production of Urea-Formalin Resin Membrane/Fragrance Microcapsules (in situ Polymerization Method)

10% of a urea resin monomer (reagent grade, manufactured by Nissan Chemical Industries, Ltd.), 2% of a resorcin resin monomer (reagent grade, manufactured by Mitsui Chemicals, Inc.), and 3% of an ethylene maleic anhydride resin (Scripset-520, manufactured by Monsanto Company) are dissolved in 85% of water, and the solution is adjusted to pH 3 using acetic acid.

50 parts of the thus obtained aqueous solution is heated to 60° C., 40 parts of the same encapsulation material as the example 1 is added and emulsified, and stirring is conducted for approximately 30 minutes, until oil droplets with an average particle size of 3 µm had been formed. To this emulsion is added 10 parts of formaldehyde, and stirring is then continued for 2 hours, thus generating a urea-formalin resin around the periphery of the encapsulation material, and forming a microcapsule slurry with a solid fraction concentration of approximately 40%.

Example 5

Production of Gelatin-Gum Arabic Membrane/Fragrance Microcapsules (Coacervation Method)

Gelatin (APH, manufactured by Nitta Gelatin Inc.) is dissolved in water to produce an aqueous solution with a gelatin concentration of 3.6%, and the solution is adjusted to pH 6 using acetic acid. To 30 parts of this aqueous solution is added 25 parts of a 3.6% aqueous solution of gum Arabic (reagent grade, manufactured by Gokyo Trading Co., Ltd.), thereby preparing an aqueous solution for forming the microcapsule membrane. 55 parts of this aqueous solution is heated to approximately 60° C., the pH is adjusted to 5, 40 parts of the same encapsulation material as the example 1 is added and emulsified, and stirring is continued until oil droplets with an average particle size of approximately 5 µm had been formed.

The resulting emulsion/dispersion is cooled gradually to 10° C., thus generating a gelatin-gum Arabic polymer membrane around the periphery of the encapsulation material. 5 parts of a 25% aqueous solution of glutaraldehyde (reagent grade, manufactured by Daicel Chemical Industries, Ltd.) is then added, and the polymer membrane is cured, thus yielding a microcapsule slurry with a solid fraction concentration of approximately 40%.

Comparative Example 1

With the exception of altering the encapsulation material (A) to 100% of the mint fragrance, a microcapsule slurry with a solid fraction concentration of approximately 40% is prepared in the same manner as the Example 1.

Comparative Example 2

An encapsulation material (A) is prepared by mixing 75% of the mint fragrance and 25% of phthalic acid (melting point: 234° C.) at 240° C., thereby dissolving the phthalic acid in the mint fragrance and forming a mixture. The melting point range for the thus obtained mixture is from 60 to 90° C. The mixture is held at 90° C. or higher to prevent it solidifying prior to emulsification.

An attempt is made to capsulate the encapsulation material in the same manner as the example 1, with the temperature of the emulsion accelerator liquid (B) held at as high a temperature as possible (90° C. or higher), but during the emulsification step, the mixture solidified and precipitated out, meaning an emulsion could not be obtained, and capsulation could not be completed.

Comparative Example 3

An encapsulation material (A) is prepared by mixing 75% of the mint fragrance and 25% of diethyl phthalate (fixative, melting point: −40° C.), thus forming a liquid mixture. This mixture remained a liquid even at −20° C. Using this liquid, microcapsulation is conducted in the same manner as the example 1, yielding a microcapsule slurry with a solid fraction concentration of approximately 40%.

Comparative Example 4

The non-capsulated, neat mint fragrance liquid (100%) is used for comparison.

Using the microcapsules obtained in the examples 1 to 5 and the comparative examples 1 and 3, as well as the neat fragrance liquid from the comparative example 4, the following evaluations are conducted.

(1) Capsulation Achievability

Mixtures for which capsulation is possible are evaluated as "A", and those for which capsulation is impossible evaluated as "C".

(2) Strength of Aroma Immediately Following Printing 50 parts of the obtained microcapsule slurry are added to 50 parts of a water-based binder (Vondic 1980NS, a water-dispersed urethane resin, manufactured by Dainippon Ink and Chemicals, Incorporated, solid fraction: 45%), thus forming a water-based screen ink.

This ink is printed onto high quality paper using a 100-mesh screen plate made of a PET Film (Tetlon®, manufactured by Teijin DuPont Films, print surface area: 3 cm×3 cm), and then dried for 24 hours at room temperature.

The surface of each of the printed materials is scratched lightly with fingernails using 10 back and forth movements, and the strength of the mint aroma is evaluated. Because the comparative example 4 is simply the neat fragrance liquid, it could not be mixed with the water-based binder, and so the aroma of the neat liquid is evaluated.

Evaluation is conducted by sensory assessment using a mixed gender panel of 5 panelists. The printed material is brought gradually closer to the nose, the maximum distance (cm) at which the aroma could be detected is measured, and then points are awarded based on the following criteria. 12 cm or greater: 5 points (the aroma is detectable even when 12 cm or further from the nose), 9 cm or greater but less than 12 cm: 4 points, 6 cm or greater but less than 9 cm: 3 points, 3 cm or greater but less than 6 cm: 2 points, 0 cm or greater but less than 3 cm: 1 point, and 0 points if the aroma is undetectable even on contact (even at 0 cm). The maximum possible score is 25 points.

(3) Strength of Aroma After Standing for 1 Week at 40° C. Following Printing

Each of the printed materials from (2) above is left to stand for 1 week at 40° C., and then, once again, the surface of the printed material is scratched lightly with fingernails using 10 back and forth movements, and the strength of the mint aroma is evaluated in the same manner as described in (2) above.

(4) Stability within Organic Solvent

Each of the produced microcapsule slurries is powdered using a spray dryer, yielding a microcapsule powder.

30 parts of this powder is added to 70 parts of toluene, and the mixture is stored in a sealed container for 1 week at 25° C. Subsequently, the toluene is evaporated off under room temperature conditions. In the case of the comparative example 4, 30 parts of the neat fragrance liquid is added directly to 70 parts of toluene.

The microcapsules remaining after the evaporation are ruptured by scratching lightly with fingernails using 10 back and forth movements, and the strength of the aroma is evaluated in the same manner as described in (2) above.

The results obtained are shown in Table 1.

TABLE 1

| | Capsulation achievability | Strength of aroma immediately after printing | Strength of aroma following 1 week at 40° C. | Stability in organic solvent |
|---|---|---|---|---|
| Example 1 | A | 21 | 19 | 19 |
| Example 2 | A | 21 | 20 | 19 |
| Example 3 | A | 20 | 18 | 18 |
| Example 4 | A | 21 | 19 | 18 |
| Example 5 | A | 22 | 15 | 14 |
| Comparative Example 1 | A | 22 | 7 | 7 |
| Comparative Example 2 | C | — | — | — |
| Comparative Example 3 | A | 22 | 9 | 8 |
| Comparative Example 4 | — | 25 | 1 | 0 |

As is evident from Table 1, the microcapsules of the Examples 1 to 5 enabled the aroma of the fragrance to be favorably retained. This is because at conditions of 40° C., the encapsulated material is a semisolid, enabling the volatility of the fragrance to be suppressed. Furthermore, the microcapsules also exhibited no interaction with the toluene of the external phase, and are able to be mixed in a stable manner.

In contrast, in both the Comparative Examples 1 and 3, because the encapsulated material is a liquid, it gradually escaped through the fine pores in the melamine resin membrane, meaning the aroma could not be retained over an extended period. Furthermore, in the organic solvent, it is thought that because the encapsulated material is a liquid, a mechanism that seeks to achieve co-solubility with the toluene draws the liquid fragrance out into the external phase.

In the comparative Example 4, the neat fragrance liquid volatilized at the same time as the evaporation of the toluene.

The comparative example 3 represents an example in which a conventionally used fixative is used to suppress volatilization of the fragrance and prolong the retention of the aroma. Examples of typical fixatives include benzyl alcohol (melting point: 15° C.), benzyl benzoate (melting point: 21° C.), triethylene citrate (melting point: −55° C.), and dipropylene glycol (melting point: −40° C.), and all of these have a melting point lower than 25° C., meaning they are unable to form a semisolid in the range from −20 to 60° C.

In the comparative example 2, although the encapsulation material needed to remain a liquid during the emulsification step of the microcapsulation, it is thought that microcapsulation could not be achieved because it proved impossible to maintain the temperature of both the emulsion accelerator liquid and the emulsion at a temperature exceeding the upper limit temperature (T2=90° C.) for the mixture melting point range.

The evaluation score for the example 5 is lower than those for the examples 1 to 4, and it is thought that this reflects the fact that the airtightness of the gelatin-gum Arabic of the capsule membrane is lower than that of both the melamine resin and the urea-formalin resin. However, the results for the example 5 are still vastly superior to those of the comparative examples.

Consumer Product Examples

The following definitions are used in the consumer product examples that are given below. Any of the consumer product examples given below may comprises one or more of the microcapsules that is claimed or disclosed in this specification.

| | |
|---|---|
| LAS | Sodium linear $C_{11-13}$ alkyl benzene sulphonate. |
| CxyAS | Sodium $C_{1x}$-$C_{1y}$ alkyl sulfate. |
| CxyEzS | $C_{1x}$-$C_{1y}$ sodium alkyl sulfate condensed with an average of z moles of ethylene oxide. |
| CxEOy | Cx alcohol with an average of ethoxylation of y |
| QAS | $R_2 \bullet N + (CH_3)_2(C_2H_4OH)$ with $R_2 = C_{10}$-$C_{12}$ |
| Soap | Sodium linear alkyl carboxylate derived from a 80/20 mixture of tallow and coconut fatty acids. |
| Silicate | Amorphous Sodium Silicate ($SiO_2$:$Na_2O$ ratio = 1.6-3.2:1). |
| Zeolite A | Hydrated Sodium Aluminosilicate of formula $Na_{12}(AlO_2SiO_2)_{12} \bullet 27H_2O$ having a primary particle size in the range from 0.1 to 10 micrometers (Weight expressed on an anhydrous basis). |
| (Na—)SKS-6 | Crystalline layered silicate of formula $\delta$-$Na_2Si_2O_5$. |
| Citrate | Tri-sodium citrate dihydrate. |
| Citric | Anhydrous citric acid. |
| Carbonate | Anhydrous sodium carbonate. |
| Sulphate | Anhydrous sodium sulphate. |
| MA/AA | Random copolymer of 4:1 acrylate/maleate, average molecular weight about 70,000-80,000. |
| AA polymer | Sodium polyacrylate polymer of average molecular weight 4,500. |
| PB1/PB4 | Anhydrous sodium perborate monohydrate/tetrahydrate. |
| PC3 | Anhydrous sodium percarbonate [2.74 $Na_2CO_3 \bullet 3H_2O_2$] |
| TAED | Tetraacetyl ethylene diamine. |
| NOBS | Nonanoyloxybenzene sulfonate in the form of the sodium salt. |
| DTPA | Diethylene triamine pentaacetic acid. |
| HEDP | Hydroxyethane di phosphonate |
| HEDMP | Hydroxyethane di (methylene) phosphonate |
| DETPMP | Diethyltriamine penta (methylene) phosphonate |
| EDDS | Na salt of Ethylenediamine-N,N'-disuccinic acid, (S,S) isomer |
| Protease | Proteolytic enzyme sold under the tradename Savinase ®, Alcalase ®, Everlase ®, by Novozymes A/S, Properase ®, Purafect ®, Purafect MA ® and Purafect Ox ® sold by Genencor and proteases described in patents WO 91/06637 and/or WO 95/10591 and/or EP 0 251 446. |
| Amylase | Amylolytic enzyme sold under the tradename Purastar ®, Purafect Oxam ® sold by Genencor; Termamyl ®, Fungamyl ® Duramyl ®, Stainzyme ® and Natalase ® sold by Novozymes A/S. |
| Lipase | Lipolytic enzyme sold under the tradename Lipolase ® Lipolase Ultra ® by Novozymes A/S. |
| Cellulase | Cellulytic enzyme sold under the tradename Carezyme ®, Celluzyme ® and/or Endolase ® by Novozymes A/S or a Glucanase enzyme |

| | |
|---|---|
| Pectate Lyase | Pectawash ®, Pectaway ® sold by Novozymes |
| Mannanase | Mannaway ® sold by Novozymes |
| CMC or HEC or EMC | Carboxymethyl or Hydroxyethyl or ester modified cellulose. |
| SS Agglom. | 12% Silicone/silica, 18% stearyl alcohol,70% starch in granular form [suds suppressor agglomerate]. |
| TEPAE | Tetraethylenepentaamine ethoxylate. |
| Photobleach | Sulfonated zinc phtalocyanine |
| Microcapsule | Aqueous slurry containing perfume loaded capsules |
| pH | Measured as a 1% solution in distilled water at 20° C. |
| MEA borate | Monoethanolamine borate |
| HCl | Hydrogen Chloride |
| SRP | Soil Removal Polymer |
| PVNO | polyvinylpyridine N-oxide |

Example #6

Bleaching high duty laundry detergent compositions are prepared:

| | I | II | III | IV | V | VI | VII | VIII |
|---|---|---|---|---|---|---|---|---|
| Blown Powder | | | | | | | | |
| Zeolite A | 13.65 | 13.65 | — | — | — | — | — | — |
| Na Sulfate | 22.67 | 22.67 | 24.43 | 30.13 | — | — | — | — |
| LAS | 6.21 | 6.21 | 5.65 | — | — | — | — | — |
| QAS | — | — | — | 2.95 | — | — | — | — |
| MA/AA | 1.42 | 1.42 | 3.50 | 4.25 | — | — | — | — |
| EDDS | 0.19 | 0.19 | 0.19 | 0.23 | — | — | — | — |
| Brightener | 0.07 | 0.07 | 0.06 | 0.08 | — | — | — | — |
| Mg Sulfate | 0.65 | 0.65 | 0.39 | 0.48 | — | — | — | — |
| HEDMP | 0.17 | 0.17 | 0.17 | 0.21 | — | — | — | — |
| Agglomerate 1 | | | | | | | | |
| QAS | — | — | 0.9 | — | — | — | — | — |
| Carbonate | — | — | 2.45 | — | — | — | — | — |
| Na Sulfate | — | — | 2.45 | — | — | — | — | — |
| Agglomerate 2 | | | | | | | | |
| $C_{14-15}EO_7$ | — | — | 2.79 | 2.21 | — | — | — | — |
| Na Sulfate | — | — | 6.65 | 6.84 | — | — | — | — |
| Agglomerate 3 | | | | | | | | |
| LAS | — | — | — | — | 13.63 | 14.96 | — | 13.63 |
| Zeolite A | — | — | — | — | 21.42 | 23.51 | — | 21.42 |
| Agglomerate 4 | | | | | | | | |
| LAS | — | — | — | — | — | — | 8.12 | — |
| Na Sulfate | — | — | — | — | — | — | 23.54 | — |
| Na Carbonate | — | — | — | — | — | — | 8.12 | — |
| Dry additives | | | | | | | | |
| LAS | — | — | 6.40 | — | — | — | — | — |
| MA/AA (particle) | — | — | 0.89 | 0.89 | 0.95 | 0.95 | 0.99 | 0.95 |
| TAED | 3.58 | 3.58 | 3.80 | 2.70 | 5.89 | 5.89 | 6.14 | — |
| NOBS | — | — | — | — | — | — | — | 5.50 |
| LAS (flakes) | — | — | — | 27.0 | — | — | — | — |
| Silicate R 2.0 | 3.85 | 3.85 | 3.85 | 2.80 | — | — | — | — |
| Citric/Citrate | 3.58 | 3.58 | 3.58 | 3.58 | 3.80 | 3.80 | 3.96 | 3.80 |
| Na Carbonate | 7.72 | 7.72 | 13.84 | — | 12.35 | — | 12.87 | 12.35 |
| HEDP | — | — | — | — | 0.48 | 0.48 | 0.50 | 0.48 |
| PC3 or PB1 | 11.01 | 11.01 | 11.01 | 8.00 | 8.55 | 8.55 | 8.91 | 8.55 |
| Protease | 0.009 | 0.009 | 0.009 | 0.009 | 0.039 | 0.039 | 0.039 | 0.039 |
| Amylase | 0.005 | 0.005 | 0.005 | 0.005 | 0.013 | 0.013 | 0.013 | 0.013 |
| Lipase | — | — | — | — | 0.002 | 0.002 | 0.002 | 0.002 |
| Pectate lyase | — | — | — | — | 0.003 | 0.003 | 0.003 | 0.003 |
| Cellulase | 0.003 | — | 0.001 | — | 0.0005 | — | — | — |
| SS agglom. | 0.36 | 0.36 | 0.36 | 0.55 | 0.62 | 0.62 | 0.64 | 0.62 |
| Soap | 0.40 | 0.40 | 0.40 | 0.40 | 0.48 | 0.48 | 0.50 | 0.48 |
| Brightener | — | — | — | — | 0.10 | 0.10 | 0.10 | 0.10 |
| Na Sulfate | 4.48 | 4.48 | — | 14.30 | 22.85 | 14.90 | 14.30 | |
| Spray-on | | | | | | | | |
| $C_{12-14}EO_7$ | 4.00 | 4.00 | — | — | 3.00 | 3.00 | 1.00 | 3.00 |
| Microcapsule 1 | 0.8 | 2.0 | 1.5 | 0.7 | 1.2 | 0.3 | 0.2 | 0.1 |
| Microcapsule 2 | — | — | — | — | 0.5 | 1.0 | — | — |
| Density (g/L) | 600 | 600 | 600 | 600 | 800 | 800 | 800 | 800 |

Example #7

The following laundry compositions, which can be in the form of granules or tablet, are prepared according to the present invention.

| Base Product | I | II | III | IV | V |
|---|---|---|---|---|---|
| $C_{14}$-$C_{15}$ AS/Tallow AS | 8.0 | 5.0 | 3.0 | 3.0 | 3.0 |
| LAS | 8.0 | — | 8.0 | — | 7.0 |
| $C_{12}C_{15}AE_3S$ | 0.5 | 2.0 | 1.0 | — | — |
| $C_{12}C_{15}AE_5/AE_3$ | 2.0 | — | 5.0 | 2.0 | 2.0 |
| QAS | — | — | — | 1.0 | 1.0 |
| Zeolite A | 20.0 | 18.0 | 11.0 | — | 10.0 |
| (Na-)SKS-6 (I) (dry add) | — | — | 9.0 | — | — |
| MA/AA | 2.0 | 2.0 | 2.0 | — | — |
| AA polymer | — | — | — | — | 4.0 |
| Citrate | — | 2.0 | — | — | — |
| Citric | 2.0 | — | 1.5 | 2.0 | — |
| DTPA | 0.2 | 0.2 | — | — | — |
| EDDS | — | — | 0.5 | 0.1 | — |
| HEDP | — | — | 0.2 | 0.1 | — |
| PB1 | 3.0 | 5.0 | 10.0 | — | 4.0 |
| Percarbonate | — | — | — | 18.0 | — |
| NOBS | 3.0 | 4.0 | — | — | 4.0 |
| TAED | — | — | 2.0 | 5.0 | — |
| Carbonate | 15.0 | 18.0 | 8.0 | 15.0 | 15.0 |
| Sulphate | 5.0 | 12.0 | 2.0 | 17.0 | 3.0 |
| Silicate | — | 1.0 | — | — | 8.0 |
| Microcapsule | 0.5 | 0.2 | 1.3 | 0.7 | 2.0 |
| Protease | 0.033 | 0.033 | 0.033 | 0.046 | 0.033 |
| Lipase | 0.008 | 0.008 | 0.008 | 0.008 | 0.006 |
| Amylase | 0.001 | 0.001 | 0.001 | 0.0014 | 0.001 |
| Cellulase | 0.0014 | 0.0014 | 0.0014 | 0.01 | — |

Example #8

The following granular detergents are prepared:

| | I | II | III | IV | V | VI | VII |
|---|---|---|---|---|---|---|---|
| LAS | 7.23 | 8.46 | 6.50 | 7.09 | 11.13 | 16.0 | 16.0 |
| QAS | 0.75 | — | 0.60 | 0.60 | 1.00 | — | — |
| $C_{14-15}EO_7$ | 3.50 | 5.17 | 3.50 | 3.70 | 3.50 | — | — |
| $C_{12-14}AE_3S$ | 0.25 | — | — | — | — | 0.70 | 1.0 |
| $C_{12-14}$—$N^+(CH_3)_2(C_2H_4OH)$ | — | — | — | — | — | 0.50 | 0.50 |
| Na tripolyphosphate | 18.62 | 25.00 | 18.62 | 24.00 | 45.00 | 15.0 | 18.0 |
| Zeolite A | — | — | 0.79 | — | — | 0.18 | 0.3 |
| Citric acid | 1.29 | — | 1.29 | — | — | — | — |
| Sodium Silicate | 3.10 | 8.00 | 4.26 | 3.87 | 10.00 | 8.0 | 6.0 |
| Sodium Carbonate | 18.04 | 11.00 | 18.04 | 18.98 | 0.42 | 14..5 | 16.0 |
| Sulfate | 17.58 | 3.98 | 19.93 | 15.48 | 10.13 | 30.0 | 30.0 |
| CMC | — | — | — | — | — | 0.20 | 0.20 |
| AA/MA | 2.15 | 1.50 | 1.85 | 1.60 | 1.94 | 0.1 | 0.05 |
| AA polymer | — | — | — | — | — | — | 1.20 |
| Amine ethoxylate polymer | 0.60 | — | 0.49 | — | — | — | 1.25 |
| Cyclic polyamine polymer | 0.07 | — | 0.07 | — | — | — | — |
| Percarbonate | 13.15 | — | 10.77 | — | — | — | — |
| PB1/PB4 | — | 9.0/9.0 | — | 10.45/0 | 2.37/0 | — | — |
| TAED | 2.50 | 5.00 | 1.58 | 1.52 | 0.66 | — | — |
| DTPA | 0.34 | 0.34 | 0.37 | 0.39 | 0.24 | 0.30 | 0.30 |
| Mg Sulfate | 1.37 | 1.43 | 1.37 | 1.41 | 0.58 | — | — |
| Protease | 0.005 | 0.011 | 0.006 | — | — | 0.006 | 0.003 |
| Amylase | 0.001 | 0.003 | 0.001 | 0.001 | — | — | 0.001 |
| Cellulase | 0.0003 | 0.0002 | 0.0003 | 0.0003 | — | — | — |
| Brightener | 0.10 | 0.17 | 0.08 | 0.08 | 0.08 | 0.23 | 0.15 |
| Microcapsule 1 | 0.6 | 1.2 | 1.5 | 0.2 | 0.1 | 1.9 | 0.7 |
| Microcapsule 2 | — | — | — | 0.5 | 1.8 | — | — |

Example #9

The following granular fabric detergent compositions which provide "softening through the wash" are prepared:

| | I | II | III | IV |
|---|---|---|---|---|
| $C_{12-15}AS$ | 0.3 | 3.43 | 2.52 | 1.05 |
| LAS | 11.0 | 5.3 | 6.55 | 7.81 |
| $C_{12-14}AE_3S$ | — | 0.74 | 0.33 | — |
| LAS (mid branched) | — | — | 1.71 | 1.37 |
| $C_{14-15}EO_7$ | — | 2.00 | 2.00 | 2.00 |
| QAS | — | 1.57 | 1.20 | 1.35 |
| Citric acid | 2.5 | 1.28 | 1.28 | 1.28 |
| (Na-)SKS-6 | 4.0 | 4.71 | 4.96 | 4.71 |
| Zeolite A | 12.0 | 13.51 | 11.31 | 15.6 |
| Percarbonate | 6.5 | 9.03 | 9.03 | 10.3 |
| TAED | 1.5 | 2.48 | 2.48 | 3.22 |
| EDDS | 0.1 | 0.1 | 0.1 | 0.1 |
| HEDP | 1.2 | 0.20 | 0.20 | 0.20 |
| Smectite clay | 10.0 | — | 13.84 | — |
| Polyethylene oxide (MW approx. 300,000) | 0.2 | 0.22 | 0.22 | — |
| Microcapsule 1 | 0.5 | 0.4 | 0.3 | 1.7 |
| Microcapsule 2 | — | 0.3 | — | — |
| Protease | 0.011 | 0.009 | 0.009 | 0.009 |
| Amylase | 0.002 | 0.001 | 0.001 | 0.001 |
| Cellulase | — | 0.0006 | 0.0006 | 0.0006 |
| Na Carbonate | 25.0 | 29.68 | 30.52 | 28.30 |
| Magnesium Sulfate | 0.1 | 0.03 | 0.03 | 0.03 |
| Suds suppressor | 1.0 | 1.0 | 1.0 | 1.0 |
| EMC | — | 1.10 | 1.10 | 1.10 |
| HEC | 0.8 | — | — | — |
| Sodium sulfate | 18.0 | balance | balance | balance |

Example #10

The following liquid detergent formulations are prepared:

|  | I | II | III | IV | V | VI |
|---|---|---|---|---|---|---|
| LAS | 7.8 | 12.2 | 4.4 | 12.2 | 5.7 | 1.3 |
| Sodium alkyl ether sulfate | — | — | 14.4 | — | 9.2 | 5.4 |
| Alkyl ethoxylate | 5.7 | 8.8 | 2.2 | 8.8 | 8.1 | 3.4 |
| Amineoxide | 1.0 | 1.5 | 0.7 | 1.5 | — | — |
| Fatty acid | 5.3 | 8.3 | 3.0 | 8.3 | — | — |
| Citric acid (50%) | 1.1 | 6.8 | 2.0 | 3.4 | 1.9 | 1.0 |
| Ca and Na formate | — | — | 0.2 | — | — | — |
| Na cumene sulphonate | 0.8 | 2 | — | 2.0 | — | — |
| Borate | — | — | 1.5 | 2.4 | 2.9 | — |
| MEA borate | 1.5 | 2.4 | — | — | — | — |
| Na hydroxide | 3.2 | 3.2 | 3.0 | 4.9 | 1.9 | 1.0 |
| Ethanol | 1.4 | 1.4 | 2.5 | 1.4 | 1.5 | — |
| 1,2 Propanediol | 4.9 | 5.0 | 6.6 | 4.9 | 4.0 | — |
| Sorbitol | — | — | — | — | 4.0 | — |
| Ethanolamine | 0.5 | 0.8 | 1.5 | 0.8 | 0.1 | — |
| TEPAE | 0.4 | 0.4 | — | — | — | — |
| Protease | 0.02 | 0.028 | 0.04 | 0.028 | 0.04 | — |
| Lipase | — | — | — | — | 0.002 | — |
| Amylase | 0.001 | 0.002 | 0.0002 | 0.01 | — | — |
| PVNO | — | — | — | — | — | — |
| Brightener | 0.1 | 0.14 | 0.15 | 0.2 | 0.12 | 0.12 |
| Silicone antifoam | — | — | — | 0.05 | — | — |
| Mannanase | 0.0004 | 0.0006 | — | — | — | — |
| Cellulase | 0.0003 | 0.0002 | 0.0003 | — | — | — |
| Amine ethoxylate polymer | 0.8 | 1.3 | 1.8 | 2.1 | — | — |
| AA or MA / AA | — | — | — | — | 0.6 | 0.2 |
| DTPMP, DTPA, EDTA mixture | 0.3 | 0.3 | 0.1 | — | — | 0.1 |
| Microcapsule 1 | 0.5 | 1.9 | 0.3 | 1.2 | 0.7 | 0.5 |
| Microcapsule 2 | — | — | 0.5 | — | 0.2 | — |

Example #11

The following liquid detergent compositions which provide "softening through the wash" are prepared:

|  | I | II | III | IV | V | VI |
|---|---|---|---|---|---|---|
| LAS | 16.0 | 16.0 | 16.0 | 16.0 | 16.0 | 16.0 |
| $C_{24}EO_7$ | 2.0 | 2.0 | 2.0 | 1.2 | 1.2 | 1.2 |
| Citric acid | 2.5 | 2.5 | 2.5 | 1.5 | 1.5 | 1.5 |
| Fatty acid | 11.4 | 11.4 | 11.4 | 6.84 | 6.84 | 6.84 |
| Protease | 0.48 | 0.48 | 0.48 | 0.35 | 0.35 | 0.35 |
| Amylase | 0.13 | 0.13 | 0.13 | 0.08 | 0.08 | 0.08 |
| NA Metaborate | 1.3 | 1.3 | 1.3 | 0.79 | 0.79 | 0.79 |
| Chelant | 1.5 | 1.5 | 1.5 | 0.9 | 0.9 | 0.9 |
| Amine | — | 0.08 | 0.08 | 0.05 | — | 0.05 |
| Brightener | 0.14 | 0.14 | 0.14 | 0.09 | 0.09 | 0.09 |
| Structurant | 0.18 | 0.18 | 0.18 | 0.26 | 0.26 | 0.26 |
| Ethanol | 0.76 | 0.76 | 0.76 | 2.38 | 2.38 | 2.38 |
| 1,2 Propanediol | 8.0 | 8.0 | 8.0 | 4.82 | 4.82 | 4.82 |
| Na Hydroxide | 6.2 | 6.2 | 6.2 | 3.8 | 3.8 | 3.8 |
| Solvent | 2.0 | 2.0 | 2.0 | 1.2 | 1.2 | 1.2 |
| Silicone | 0.2 | 0.2 | 0.2 | 0.12 | 0.12 | 0.12 |
| Dispersant | 0.06 | 0.06 | 0.06 | 0.04 | 0.04 | 0.04 |
| Perfume | 0.81 | — | 0.6 | 0.48 | 0.65 | 0.40 |
| Dye | 0.004 | 0.003 | 0.005 | 0.003 | 0.003 | — |
| Bentonite clay | 3.36 | 3.36 | 3.36 | 3.36 | 3.36 | 3.36 |
| Microcapsule 1 | — | 2.0 | 0.5 | 0.7 | 0.3 | — |
| Microcapsule 2 | — | — | — | 0.3 | 1.2 | 0.7 |

Example #12

The following concentrated liquid detergent formulations are prepared:

|  | I | II | III | IV | V | VI | VII | VIII |
|---|---|---|---|---|---|---|---|---|
| MEA | 8.6 | 8.0 | 8.0 | 8.0 | 8.0 | 8.0 | 8.0 | 8.0 |
| Propanediol | 19.5 | 22.0 | 21.9 | 21.8 | 21.0 | 21.0 | 22.0 | 21.9 |
| Sulfite solution | 0.15 | 0.15 | 0.15 | 0.15 | 0.15 | 0.15 | — | — |
| $C_{24}EO_7$ | 19.6 | 19.5 | 19.6 | 19.4 | 19.8 | 19.8 | 19.8 | 19.8 |
| Brightener | 0.28 | 0.38 | — | 0.28 | 0.28 | 0.28 | 0.28 | 0.28 |
| LAS | 23.7 | 23.0 | 23.1 | 22.9 | 23.3 | 23.3 | 23.3 | 23.3 |
| Dispersant | 3.2 | 1.6 | 1.6 | 1.6 | 1.6 | 1.6 | 1.6 | 1.6 |

-continued

|  | I | II | III | IV | V | VI | VII | VIII |
|---|---|---|---|---|---|---|---|---|
| Fatty acid | 17.3 | 17.3 | 17.4 | 17.3 | 17.6 | 17.6 | 17.6 | 17.6 |
| Perfume | 1.5 | — | 1.5 | 1.6 | 0.9 | — | 1.5 | 1.6 |
| Protease | 1.16 | 1.16 | 1.16 | 1.16 | — | — | — | — |
| Amylase | — | 0.14 | 0.14 | 0.14 | — | — | — | — |
| Mannanase | — | 0.12 | 0.12 | 0.12 | — | — | — | — |
| Dye | 0.002 | 0.001 | 0.005 | 0.005 | 0.004 | 0.004 | 0.001 | 0.001 |
| Antimicrobial Agent | 0.0006 | — | — | — | — | — | — | — |
| Preservative: Glutaraldehyde | 0.001 | — | — | — | — | — | — | — |
| Bentonite clay | 0.2 | — | — | — | — | — | — | — |
| Structurant | 0.2 | — | — | — | — | — | — | — |
| Microcapsule 1 | 2.5 | 3.5 | — | 1.1 | — | 2.0 | 1.7 | — |
| Microcapsule 2 | — | — | 2.0 | 1.2 | 4.0 | 2.0 | — | 3.5 |

Example #13

The following concentrated/dilute liquid fabric softening compositions are prepared.

| Ingredients | 1 | 2 |
|---|---|---|
| Softener Active: Rewoquat V3682 from Goldschmidt | 17.61 | 5.2 |
| Silicone: Antifoaming agent: MP10 from Dow Corning | 0.01 | 0.004 |
| HEDP (Sodium salt) | 0.17 | — |
| HCl | 0.005 | 0.013 |
| SRP: Texcare 3639 from Clariant | 0.05 | — |
| CaCl₂ | 0.035 | — |
| Stabilizer: PEG-4K Pluriol E4050E | 0.50 | — |
| Preservative: gluteraldehyde 50% - from BASF | — | 0.025 |
| Perfume | — | 0.32 |
| Dye | 0.003 | 0.0006 |
| Microcapsule | 4.0 | 2.0 |
| Demineralized water | Bal. | Bal. |

Example #14

The following hair conditioners are prepared.

| Ingredient | 1 | 2 | 3 |
|---|---|---|---|
| Stearamidopropyldimethyl amine | 2.0 | 1.0 | |
| Behenyltrimethyl Ammonium Chloride | | | 3.4 |
| Quaternium 18 | | .75 | |
| PEG-2M | | .5 | |
| Emulsifying Wax | | .5 | |
| L-glutamic acid | .64 | | |
| Cetyl Alcohol | 2.5 | .96 | 2.0 |
| Stearyl Alcohol | 4.5 | .64 | 3.6 |
| Dimethicone/Cyclomethicone (15/85 blend) | | 4.2 | |
| Dimethicone | 4.2 | | 4.2 |
| Hydroxyethyl Cellulose | | .25 | |
| Glyceryl Monostearate | | .25 | |
| Additional Perfume | .3 | .2 | .2 |
| Chemitech microcapsules | .4 | | .6 |
| Chemitech microcapsules | | .4 | |
| Citric Acid | | .13 | |
| NaOH | | | .014 |
| Benzyl Alcohol | .4 | .4 | .4 |
| EDTA | .1 | .1 | |
| Kathon | .0005 | .0005 | .0005 |
| Disodium EDTA | | | .127 |

Example #15

The following shampoos are prepared:

| Component | Example No. 1 | Example No. 2 | Example No. 3 | Example No. 4 |
|---|---|---|---|---|
| Water-USP Purified & Minors | Q.S. to 100 | Q.S. to 100 | Q.S. to 100 | Q.S. to 100 |
| Ammonium Laureth Sulfate | 10 | 11.67 | 10 | 6 |
| Ammonium Lauryl Sulfate | 6 | 2.33 | 4 | 10 |
| Cocamidopropyl betaine | — | 2 | — | — |
| Cocamide MEA | — | 0.8 | 0.8 | 0.8 |
| Citric Acid | 0.04 | 0.04 | 0.04 | 0.04 |
| Sodium Citrate Dihydrate | 0.45 | 0.45 | 0.45 | 0.45 |
| Disodium EDTA | 0.1 | 0.1 | 0.1 | 0.1 |
| Kathon | 0.0005 | 0.0005 | 0.0005 | 0.0005 |
| Sodium Benzoate | 0.25 | 0.25 | 0.25 | 0.25 |
| Disodium EDTA | 0.1274 | | 0.1274 | 0.1274 |
| Cetyl Alcohol | — | 0.6 | 0.9 | 0.6 |
| Ethylene Glycol Distearate | | 1.5 | 1.5 | 1.5 |
| Polyox PEG7M | — | — | .1 | — |
| Trihydroxystearin (Thixin R, Rheox) | .25 | | | |
| Polyquaternium-10 (KG30M) | 0.5 | | 0.15 | |

-continued

| Component | Example No. | | | |
|---|---|---|---|---|
| | 1 | 2 | 3 | 4 |
| Polyquaternium-10 (LR30M) | — | — | — | .25 |
| Guar Hydroxypropyltrimonium Chloride1 | — | 0.5 | — | — |
| Dimethicone (Viscasil 330M) | — | 1.4 | — | 4.0 |
| Dimethicone microemulsion (Dow 1664) | — | — | 5.0 | — |
| Zinc Pyridinethione | — | 1 | — | — |
| Chemitech microcapsules (1) | 1 | 1.5 | .5 | — |
| Chemitech microcapsules (2) | — | — | .5 | .8 |
| Additional Perfume | 0.3 | 0.7 | 0.2 | 0.7 |
| Sodium Chloride | 0-3 | 0-3 | 0-3 | 0-3 |
| Ammonium Xylene Sulfonate | 0-3 | 0-3 | 0-3 | 0-3 |

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A consumer product comprising an acrylic polymer microcapsule;
wherein the microcapsule encapsulates a homogenous mixture comprising a volatile substance and an additive mutually dissolved within the volatile substance;
wherein the additive has a melting point from 25° C. to 200° C.;
wherein the melting point of the additive is greater than a melting point of the volatile substance;
wherein the additive has a molecular weight of less than 500 g/mol; and
wherein the homogenous mixture has a melting point range such that at least a portion of the melting point range is between about 0° C. and about 60° C. such that the homogenous mixture is in a semisolid state from about 0° C. to about 60° C.

2. The consumer product according to claim 1, wherein the at least a portion of the melting point range of the homogenous mixture is between about 10° C. and about 60° C. such that the mixture is in a semisolid state from about 10° C. to about 60° C.

3. The consumer product according to claim 2, wherein the at least a portion of the melting point range of the homogenous mixture is between about 20° C. and about 60° C. such that the mixture is in a semisolid state from about 20° C. to about 60° C.

4. The consumer product according to claim 1, wherein the volatile substance is one or more reagents selected from the group consisting of fragrances, plant-based essential oils, deodorants, and deodorizers.

5. The consumer product according to claim 1, wherein the volatile substance is selected from a fragrance consisting of a perfume, perfume mixture, and perfume systems.

6. The consumer product according to claim 1, wherein the volatile substance comprises a liquid volatile substance before being mixed with the additive.

7. The consumer product according to claim 1, wherein the additive is one or more compounds selected from the group consisting of lipophilic compound, alcohols, carboxylic acids, hydroxyl acids, and paraffin.

8. The consumer product according to claim 1, wherein the mixture comprises from 10 to 200 parts by weight of the additive per 100 parts by weight of the volatile substance.

9. The consumer product according to claim 1, further comprising an adjunct material; wherein the adjunct material is one or more materials selected from the group consisting of surfactants, builders, chelating agents, dye transfer inhibiting agents, dispersants, enzymes, enzyme stabilizers, catalytic metal complexes, bleach activators, hydrogen peroxide, sources of hydrogen peroxide, preformed peracids, photobleaches, polymeric dispersing agents, clay soil removal/anti-redeposition agents, brighteners, suds suppressors, dyes, perfumes, structure elasticizing agents, fabric softeners, carriers, hydrotropes, processing aids, solvents, and pigments.

10. The consumer product according to claim 1, wherein the consumer product is one or more products selected from the group consisting of laundry detergent compositions, laundry compositions, bleaching laundry detergent compositions, granular detergents, granular fabric detergent compositions, liquid detergent formulations, liquid detergent compositions with fabric softener, concentrated liquid detergent formulations, concentrated/dilute liquid fabric softening compositions, bleaches, cleaning products, and shampoos.

* * * * *